United States Patent

Mangubat et al.

[11] Patent Number: 5,984,936
[45] Date of Patent: Nov. 16, 1999

[54] IMPULSIVE CUTTER AND PROCESS FOR HAIR GRAFT PREPARATION

[76] Inventors: E. Antonio Mangubat, 1701 126$^{th}$ Ave. E.; Phillip J. Timm, 1324 122$^{nd}$ Ave. E., both of Edgewood, Wash. 98372

[21] Appl. No.: 09/062,194

[22] Filed: Apr. 17, 1998

[51] Int. Cl.$^6$ .......................... A61B 17/50; A61B 17/32
[52] U.S. Cl. .......................................... 606/167; 606/132
[58] Field of Search .................................. 606/132, 131, 606/167

[56] References Cited

U.S. PATENT DOCUMENTS 3,998,230  12/1976  Miller .
4,476,864  10/1984  Tezel .
5,584,841  12/1996  Rassman .
5,584,851  12/1996  Banuchi .
5,662,661   9/1997  Boudjema .

*Primary Examiner*—Michael Buiz
*Assistant Examiner*—Vy Q. Bui
*Attorney, Agent, or Firm*—Western Patent Group

[57] ABSTRACT

A device and method for producing a large number of micrografts of hair-bearing tissue in a reduced time are provided. The micrografts so produced are suitable for surgical transplantation and are seen to be both consistent in size and fertile with respect to the survival rate of the follicle-bearing tissue so transplanted.

20 Claims, 5 Drawing Sheets

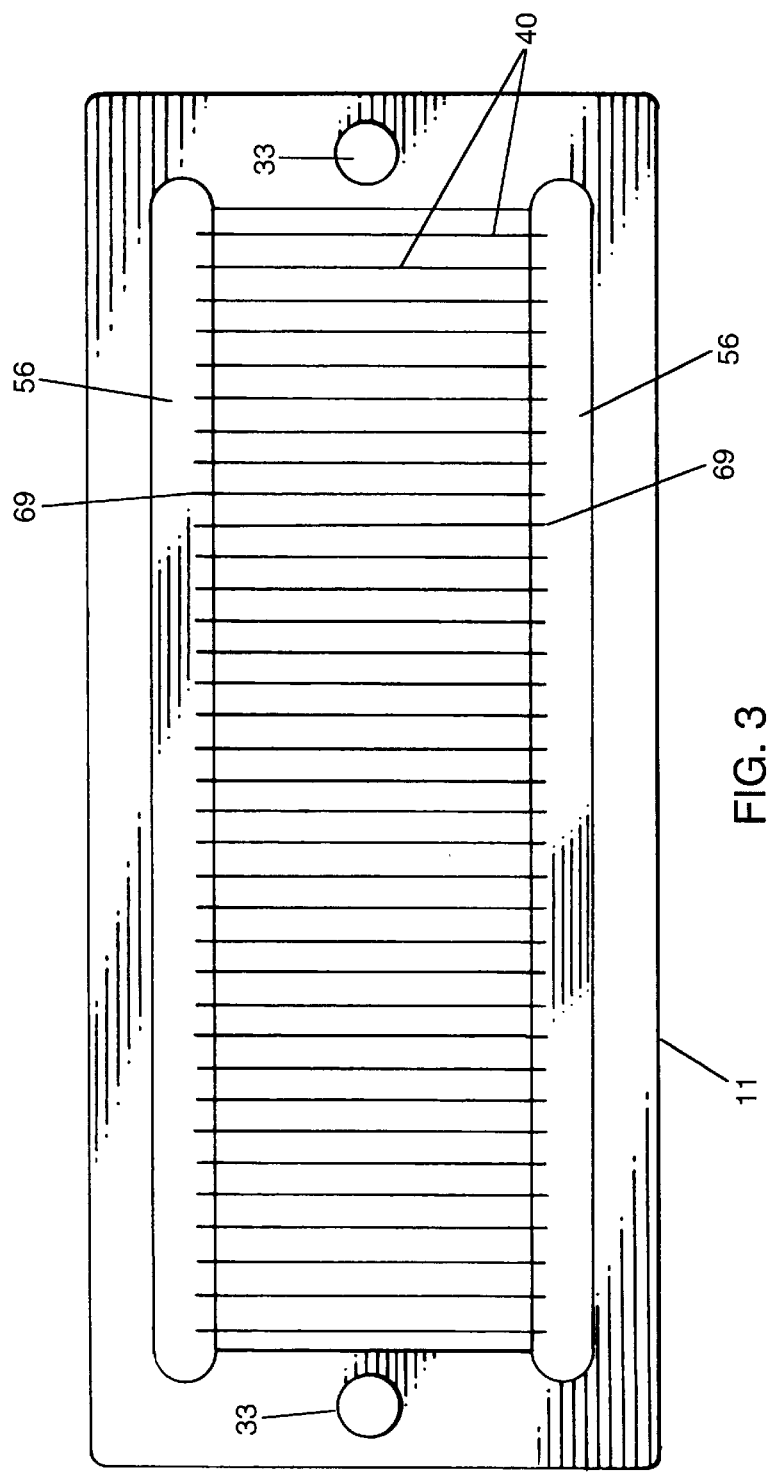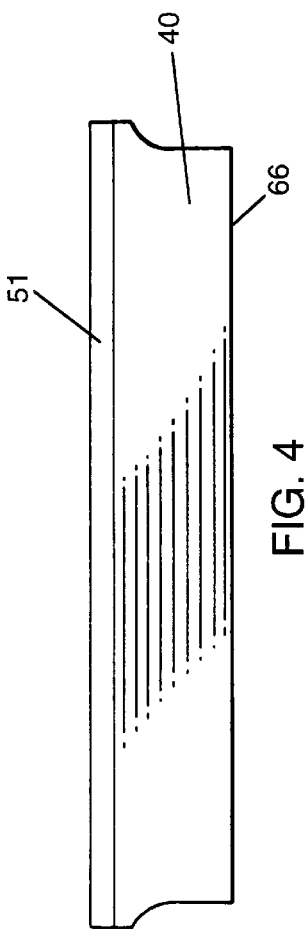

IMPULSIVE CUTTER AND PROCESS FOR HAIR GRAFT PREPARATION

BACKGROUND OF THE INVENTION

1) Technical Field

This invention relates to the art of grafting hair follicles from one area of the dermis to another, wherein the tissue bearing the hair follicles may be obtained, for example, from the occipital scalp using a specialized knife. More particularly, it relates to a tool useful in modifying raw follicle-bearing dermal sections in order to maximize the relative population of successful follicle transplantations, as well as a method for using the tool.

2) Description of Related Art

The well-known phenomenon of male pattern baldness has provided a great deal of motivation for improvements in techniques for transplanting hair follicles from one area of the body to a scalp region in which functional follicles are no longer active. Typically, hair is harvested from the back or side of the scalp to create hair grafts which are subsequently implanted in the front, top, and crown of the head. Several workers in this field have provided a wide variety of devices and methods aimed at improved graft harvesting and placement techniques, including the disclosures of U.S. Pat. Nos. 5,693,064; 5,643,308; 5,611,811; 5,611,810; 5,584,851; 5,584,841; 5,578,054; 5,562,732; 5,490,850; 5,439,475; 5,417,683; 5,273,900; and 4,243,038, the entire contents of which are herein incorporated by reference thereto.

Although there have been several advances made in recent years with regards to increasing the density of transplanted follicles and the aesthetic appeal of the configurations employed, young men undergoing hair restoration surgery may still be disappointed for several reasons, including poor graft growth, inflammation, (folliculitis), which, although typically treatable by conventional antibiotics, has in recent years been encountered in resistive strains. Additionally, transplanted hair often also kinks and curls unpredictably.

Poor graft growth is an unpredictable complication of hair transplant surgery and has been reported with every technique ever employed including round grafts, minigrafts, micrografts, strip grafts, 1-hair, and 2-hair grafts. The complication of poor graft growth is the least understood complication of this type of surgery and occurs even with the most meticulous technique in the hands of skilled surgeons.

A critical aspect of successful transplant surgery is the quality of the grafts produced. Quality is dependent on several factors including hair characteristics (i.e., color, texture, waviness) hair density, and the technique by which the grafts are produced. Of these, the characteristics and density are variables beyond the control of the surgeon. Thus the key factor in performing a successful hair transplant is the graft production technique.

Micrografts of the scalp ("donor strips") are regularly obtained from rectangular, elongated strips of occipital donor scalp containing hair follicles measuring up to about 20 cm in length and 1.0 to 2.0 mm wide and about 5 mm in depth. Donor strips are typically harvested from the occipital scalp using a specialized knife well-known to those of ordinary skill in this art to be comprised of a handle bearing at its end up to eleven parallel cutting blades spaced equidistant from each other at about 1 to 2 mm. Through use of such a knife, graft strips measuring about 1.5 mm in width and 12–16 cm in length may be obtained.

Surgeons typically harvest several parallel donor strips simultaneously. Following the harvest, technicians section the donor strips, manually, by laying the strips on a hard, flat surface and making cuts perpendicular to the overall length of the strip. Such cuts are made parallel to the direction of growth of hair from the individual follicles and are spaced such that each cut section contains between about 1 and 6 root follicles. Sections of the graft strips so obtained are subsequently implanted by surgical technique in a region of the scalp where hair loss had been encountered. Although such manual sectioning and transplanting is labor intensive whereby the costs of the manipulations passed on to the patient, the results are considered to justify the expenditure in most cases.

Accordingly, it is seen that contemporary hair transplant technique has evolved into the use of larger numbers of small grafts. To reap the benefits associated therewith, many hair transplant surgeons have gone to using micrografts, as set forth above, exclusively, to obtain natural-appearing results in shortened time frames. This has in turn resulted in an increased demand placed on the surgical team to create and place typically over one thousand grafts per patient, which is substantially greater than that of even the recent past. Accordingly, the per worker output for transplant technicians is significantly decreased by surgeons desirous of employing this most-preferred technique.

An advance in the field of transplant technology was brought forth recently by the invention of Pascal Boudjema, as described in U.S. Pat. No. 5,662,661; the contents of which are herein incorporated by reference. The '661 patent describes a device containing a plurality of equally-spaced, parallel blades having their cutting edges coincide along a common plane. In its operation, a graft strip is laid across the blades, and a clamping means is caused to slowly apply a uniform force to the graft along its entire length. The result of this undertaking is that the labor associated with the step in which perpendicular cuts are made on the graft strips mentioned above may now be carried out in a single operation, rather than in a series of individual incisions. Obviously, the number of cuts which a given technician can carry out using this method and apparatus is substantially increased over the prior method.

However, the device and process of the '661 patent is not without a major drawback, that being the damage caused to the graft strips as a result of the squeezing force applied to the graft strips in accordance with the disclosed process for which that device was intended. The application of the steadily-increasing, force relied upon by the Boudjema art for the cutting operation tends to cause crushing and distortion of the tissues within and immediately surrounding individual hair follicles, and is believed to contribute materially to the failure of a significant number of transplanted follicles to produce healthy hair following transplantation. Clearly, it would be desirable to provide a device and method which provide the increased technician capacity of the '661 patent, while at the same time producing grafts which are not damaged or distorted by the crushing forces required thereby, so as to produce a larger number of healthier grafts than are available using any other method or apparatus, including manually cut grafts. It is towards the solution of this, and the other aforementioned problems in the art that the device and process of the instant invention is directed.

Therefore, it is an object of this invention to provide a novel technique by which hair grafts having an increased graft growth rate over all prior art in this field may be produced. It is yet another object of this invention to provide a device useful in the novel technique of this invention by which transplant technician productivity may be substantially increased, particularly where larger numbers of smaller grafts are employed, without damaging the individual grafts by, for example, crushing forces.

SUMMARY OF THE INVENTION

The drawbacks associated with the prior art outlined above are substantially remedied by the instant invention, which provides a device and method whereby large numbers of healthy, small, follicle-bearing skin grafts suitable for hair transplantation to any bodily region may be produced in a minimum of time by technicians of ordinary skill. In addition, the grafts produced are of a consistent size, as dictated by the separation distance between the cutting means herein described.

The device of this invention comprises a base portion having a plurality of cutting blades contained therein, wherein the blades are arranged in a parallel configuration in which the cutting edges of the blades are coincident on the same plane. The distance between the individual blades is pre-determined, and may be either uniform or non-uniform, being determined by retaining grooves machined either in the base or in retaining bars located within the base, which hold the blades in a rigid and fixed position.

As used in the process disclosed herein, the device of this invention also comprises an impulsive force spreader means, as well as a means for locating and holding the force spreader in position. The force spreader comprises sheet stock material which is preferably essentially flat in shape and may be comprised of any one of various suitable materials including stainless steel, high impact polymeric compositions, fiber reinforced composite materials, or woods, to name but a few of the many possibilities. The impulsive forces spreader substantially equalizes the magnitude of the impulsive forces generated in accordance with the instant process along the entire length of a graft strip subject to rapid incision encountered when processed according to the procedure disclosed herein.

In operation of the device, a surgeon first produces a donor strip, which is subsequently sectioned into individual graft strips. A single graft strip is then laid upon the blades' cutting edges with the length dimension of the strip being substantially perpendicular to the length of the individual cutting blades. The direction of growth of the hair follicles is then made to coincide with the parallel blades by manually adjusting the position of the graft strip. This is important to ensure that the final cuts in the graft strips are essentially parallel with the direction of hair growth from follicles adjacent to the cuts. Next, the impulsive force spreader is placed in its proper position with the assistance of locating means, atop the graft strip. At this stage, impulsive force is applied to the force spreader which is then mechanically transmitted to the graft strip thus causing the graft strip to be cleanly incised at several intervals along its length, coincident with the location of the blades upon which the strip has rested. The force spreader and graft strip are then simultaneously removed from the device, and the graft strip is subsequently separated into grafts each containing between about 1 and 6 hair follicles per graft. These grafts are then surgically transplanted into a patient's scalp.

BRIEF DESCRIPTION OF THE DRAWINGS

In the annexed drawings:

FIG. 3 is a top view of the device of this invention, less the force spreading means, showing the location of the retaining bars and the slotted grooves therein which serve to secure the cutting blades at specific intervals in place within the device.

FIG. 4 is a side view of one of the cutting blades used in the device of this invention.

DETAILED DESCRIPTION

The present invention provides a device and process whereby a large number of hair grafts each containing between about one and five follicles each (hereinafter "micrografts", having 1–2 hairs per graft and "minigrafts", having 3–5 hairs per graft) may be produced in a relatively short time frame compared with prior art methods. Furthermore, the grafts produced in accordance with the process disclosed herein possess superior structural integrity over prior art methods and are thus associated with a decreased tendency for follicular damage and an increased probability of producing viable hair-bearing follicles subsequent to their having been transplanted.

By exhaustive experimentation the inventors hereof have discovered that grafts possessing these qualities may be produced using controlled impulsive forces, through the instant device.

Impulse is a phenomenon known to physicists as the product of net force and the time during which it acts, and equals the change in momentum of a body involved in a collision. Impulse is readily derived from Newton's Second Law of Motion and is measured in units of force multiplied by time, such as Newton*seconds or pound*seconds. Impulsive forces which are commonly exerted are known to be extremely high. For example, the impulse acting on a 0.35 lb baseball travelling at 90 ft./sec. which is struck by a bat sufficiently to cause the ball to travel in a direction opposite to the initial at 110 ft./sec. is −2.2 lb.*sec. However, if the time through which the impulse acts is 0.001 sec., the force acting on the ball is −2200 pounds. In the instant invention, impulsive forces are controllably caused to act upon the graft strips through use of the instant device, to effect precision cuts of the graft strips.

Figure 2:
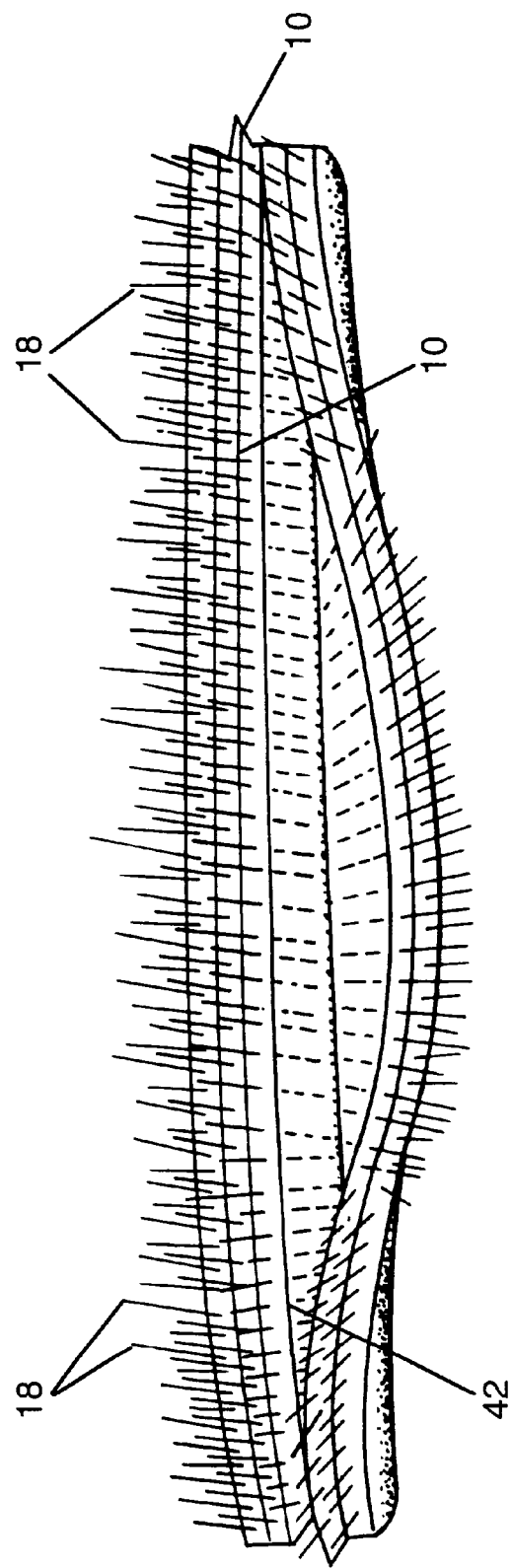
FIG. 2 is a perspective view of a donor strip from which several graft strips may be obtained.
Figure 5:
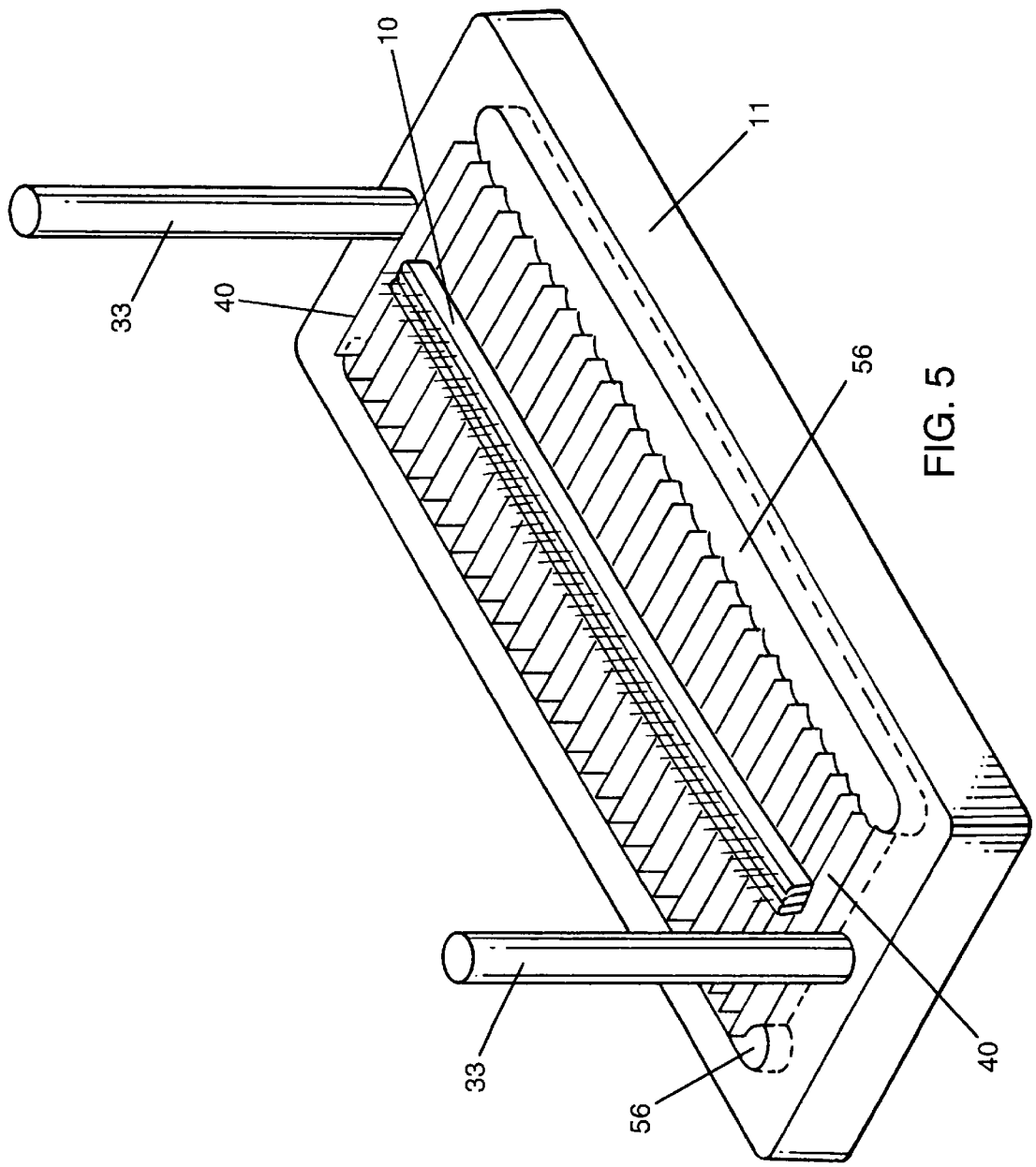
FIG. 5 is a perspective view of the device of the invention, less the force spreader, and with a graft strip in its functional location prior to cutting.

To produce the graft strips provided for by the instant device and process, one must first provide a donor section, as pictured in FIG. 2 having parallel longitudinal cuts 42, and showing the direction of growth of hairs 18 with respect to the donor graft overall. From such a donor section a graft strip measuring between about 1.0 to 2.0 mm wide and up to 20 mm in length is procured through skilled use of a multi-bladed scalpel. The graft strip is laid across the sharp edges of the cutting means (blades) 40, carefully aligning the growth direction of hair from the follicles with the cutting means as shown in FIG. 5. Next, preferably, a sterile graft holding means, 27 of FIG. 6, such as preferably a wooden tongue depressor or the like having dimensions sufficient to completely cover said graft strip is placed over the graft strip. Subsequently, the force spreading means 24 is placed over the graft holding means and held in place by locators 33 or by manual pressure. Preferably, the force spreading means and the graft holding means are of the same physical dimensions. Force spreading means 24 is gently placed atop the graft holding means in so that the force spreading means and graft strip are in effective mechanical contact with one another, taking extra care not to apply any substantial pressure to the graft strip which would tend to cause the type of damage to the graft as is encountered in the prior art. Finally, an impulsive force is applied to the graft strip, preferably by a blow with a hammer, such as a rhinoplasty hammer or similar device to the centermost portion of the impulsive forces spreader. Preferably, at the hands of a surgeon who has been properly instructed or has sufficient experience with the device, meticulous multiple strikes with a hammer or other device at several positions along the entire length of the forces spreader have been discovered to be particularly advantageous. The impulsive forces so delivered cause immediate precise laceration of the graft strip, which instantly produces a plurality of superior micrografts suitable for implantation and which have an extremely high likelihood of bearing hair upon subsequent surgical implantation.

Figure 1:
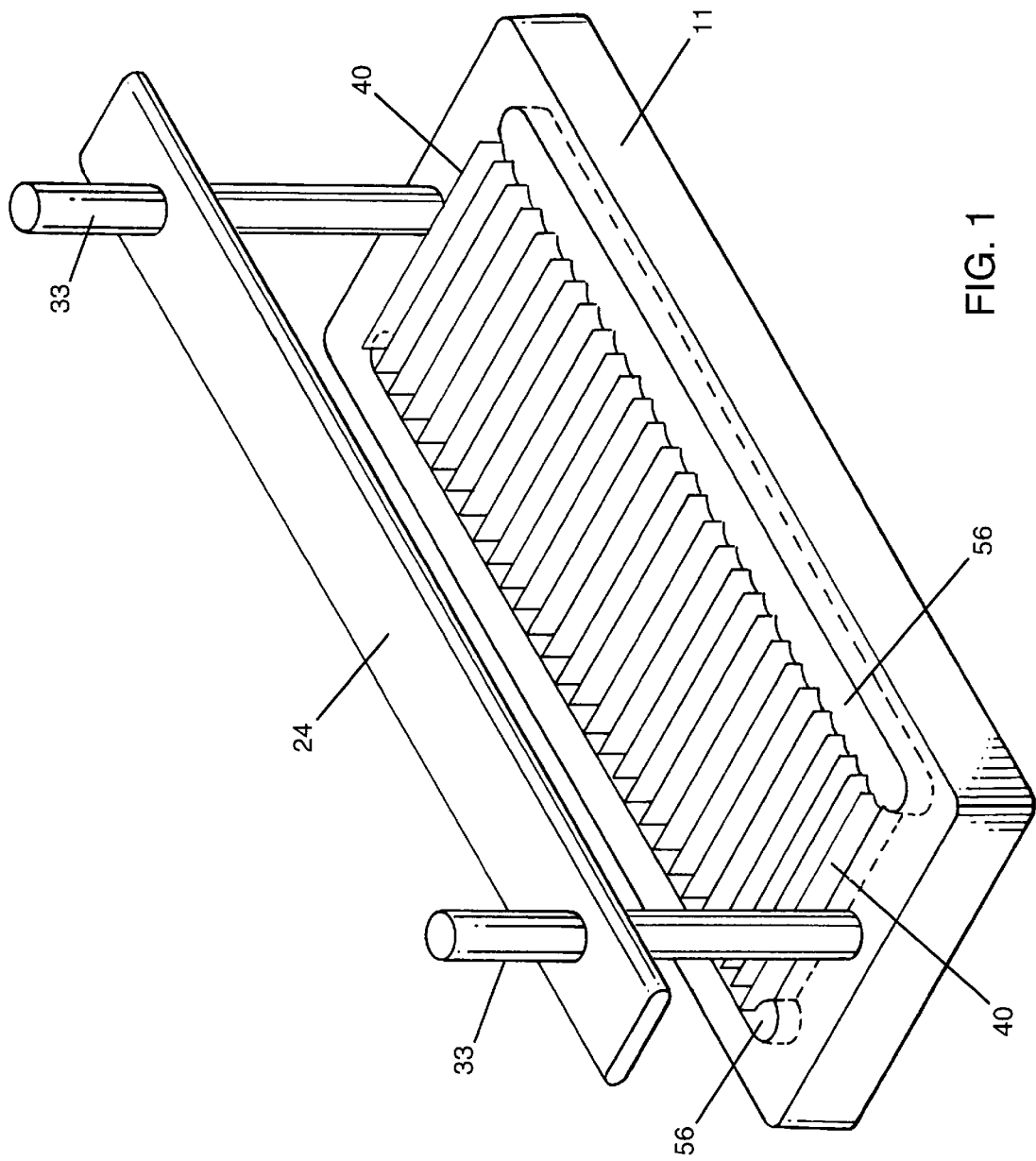
FIG. 1 is a perspective view of the device of this invention.

Referring to the drawings, and initially to FIG. 1 there is illustrated a perspective view of the complete assembled impulsive forces graft cutting device of this invention. The impulsive graft cutter pictured therein comprises a base portion 11, a cutting means which preferably includes a plurality of cutting blades 40, and retaining bars 56 into which are machined grooves useful for holding the cutting blades securely in place within the base portion. Retaining bars 56 are removable from base portion 11 in order that the apparatus may be cleaned and sterilized between procedures. FIG. 3 depicts the machining in the retaining bars 56 as evident from the positions of the ends of blades 40 within the machined grooves 69 of the retaining bars.

There is also force spreading means 24, and, in the most preferred form of the invention, at least one locating means 33 for positioning the force spreading means in a desired location.

While the base portion of this invention may in principle take on any physical shape, provided that there is provision for holding the plurality of cutting means herein disclosed in their required positions, the most preferable configuration of the base portion is that of an essentially rectangular-solid having an upper face and a lower face. In practice, the lower face is in contact with a surface upon which the completed device as a whole rests. Into the upper face of the preferable configuration of the base portion is provided, by machining, for example, an essentially rectangular shaped open cavity having a depth sufficient for accommodating the plurality of cutting means and retaining bars, when used. Preferably, the base portion is about six inches long, four inches wide and about ¾ inch thick. The depth of the machined cavity is about ⅜ inch. Such a depth, in conjunction of the width dimension of the cutting means employed provides that the cutting means preferably protrudes between about 1/16 and ¼ inches above the upper face of the base portion. The base portion consists in a means for holding a plurality of cutting blades in a fixed position in order that the blades do not substantially move when subjected to an impulsive force delivered through a graft strip subsequently placed across the blades as shown in FIG. 5. The base portion may itself contain machined grooves or channels in one or more of the inner walls of the cavity portion into which are placed, by sliding into position, the cutting blades. However, in the most preferred form of the invention, retaining bars 56 are utilized for this purpose. The base portion may be constructed of any material which is not adversely affected by the impulsive forces normally encountered through use of the device, and is preferably made from surgical stainless steel. Other suitable materials include, but are not limited to: other metallic alloys, fiber reinforced composites including fiberglass or graphitic composites, high impact polymers, wood, etc. Preferably, the distance between the cutting edges of the blades is between about 0.5 and 10 millimeters, and every whole integer therebetween, with 1.0, 1.25, and 1.5 mm being especially preferred. More preferably, the distance between the cutting edges of the blades is between about 0.5 and 5 millimeters, and most preferably, the distance between the cutting edges of the blades is between about 1 and 4 millimeters.

As already mentioned, retaining bars 56 are not essential to the functionality of the instant device, but serve as a convenient means for quick and easy removal of the cutting blades 40 which are held in position in the finished device hereof by grooves machined into a face portion of a given retaining bar. It has been discovered also that by placing shims of varying thicknesses in the space between the retaining bar and base portion that the tension in the blades may be conveniently adjusted to a desired level. The materials of construction from which the retaining bars may be made include those already set forth for the base.

Figure 6:
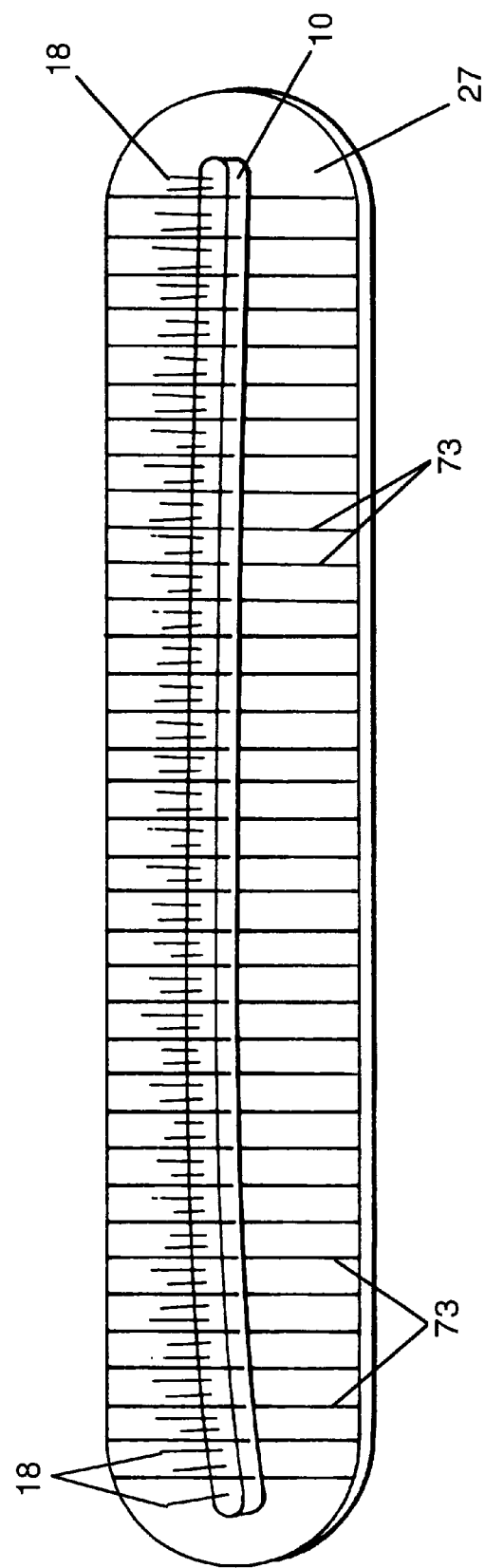
FIG. 6 is a top view of a graft strip after the cutting operation, showing the follicular alignment with the incisions effected by the blades from the device according to the process disclosed herein.

The impulsive forces spreader 24 is preferably composed of surgical stainless steel having a thickness of at least 1.5 mm in order that it does not undergo substantial deformation after being repeatedly subjected to the impulsive forces encountered in the instant process. The function of the impulsive forces spreader is to disperse the impulsive forces evenly across the graft strip to produce evenly cut sections as shown in FIG. 6. In practice this has been found to be extremely effective, provided that the forces spreader retains an essentially flat configuration. Materials from which the forces spreader may be constructed include those already mentioned for the base and retaining bar portions.

The locators 33 for the forces spreader are preferably posts, as shown in the various Figures. However, other equivalent means for locating the forces spreader in an identical position for each time the device is used are now herein indicated as being useful for the instant invention, and these include various pins and machined grooves whether located in the base portion 11 or the forces spreader 24 itself.

The cutting means useful for the instant device and process may be any blade, edge, or surface known as being useful for cutting flesh or tissues by those of ordinary skill in the medical arts, but also may comprise common knives, razor blades, or the like. Preferably, though, the blades are of the type shown in FIG. 4, having a cutting edge 66 and a tab portion 51 useful in assisting location of the blade in rigid position through use of grooves machined in the retaining bar means or into the body of the base itself. A variety of shapes are thus anticipated as being possible, including those where the length of the cutting portion is greater than, less than, or equal to that of the tab portion.

Although in the various figures the edges of the cutting means 40 are depicted as being flush with the upper surface of base portion 11, in the most preferred form of the invention, the common plane formed by coincidence of the cutting edges of the cutting means is elevated between about 1 mm and 10 mm above the upper surface of the base portion.

The figures and description have shown a single graft strip in position, as in FIG. 5, the instant device is extremely well-suited for producing several micrografts simultaneously, by laying several graft strips 10 across cutting means 40 in an arrangement wherein the graft strips are essentially parallel to one another. The only requirements of producing micrografts from several graft strips simultaneously are to provide an impulsive forces spreader which is of sufficient dimension to cover the graft strips, and to supply the force sufficient to produce the proper cuts. The impulse typically required to produce the cuts desired is between about 0.06 and 2.5 Newton*sec. for a graft strip measuring 1.5 mm wide and 18 mm long. Since the actual time which the force acts on the strip is estimated to be approximately 0.005 sec., it is apparent that the acting forces are indeed high.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

We claim:

1. A device for rapidly producing a large number of structurally intact, healthy grafts of follicle-bearing skin tissue useful for surgical implantation which comprises:
   a) an essentially rectangular-solid shaped base portion having an upper face and a lower face, outer wall portions, and a rectangular open cavity in its upper face having inner wall portions disposed therein;
   b) means for receiving and securely holding a plurality of cutting means parallel to one another;
   c) a plurality of cutting means located within said means for receiving and securely holding, wherein at least one edge of each of said plurality of said cutting means coincide on a common horizontal plane;
   d) a planar impulsive force spreading means; and
   e) a locating means for positioning said planar impulsive forces spreading means in a stationary position above said cutting means, said locating means comprising at least two guiding posts adapted to receive said force spreading means, wherein said guiding posts extend perpendicularly from said base portion and wherein said locating means only permits motion of said planar impulsive force spreading means in a direction 90 degrees to the common horizontal plane defined by said at least one edge of each of said plurality of said cutting means.

2. The device of claim 1 wherein said horizontal plane is essentially parallel to said upper face of said base portion.

3. The device of claim 1 wherein the distance between each of said plurality of cutting means is uniform and is between about 0.5 mm and 10 mm.

4. The device of claim 1 wherein said means for receiving and securely holding includes at least one retaining bar, wherein said retaining bar is substantially rectangular solid in shape and comprises at least one face portion.

5. The device of claim 4 wherein said retaining bar has a plurality of channels machined into at least one of its face portions.

6. The device of claim 1 wherein said means for receiving and securely holding includes a plurality of channels for receiving said plurality of cutting means in at least one inner wall portion of said base portion.

7. The device of claim 6 wherein said channels are oriented coincident with the thickness measurement of said base portion.

8. A process for rapidly producing a large number of structurally intact, healthy micrografts of follicle-bearing skin tissue useful for surgical implantation which comprises the steps of:
   a) providing at least one graft strip of follicle-bearing tissue;
   b) contacting said graft strip with a plurality of cutting means, said cutting means having cutting edges which coincide on a common first horizontal plane, wherein said cutting means are held in a stationary position by virtue of their being located within a base portion adapted to contain said cutting means, said base portion further including at least two guiding posts adapted to receive an impulsive force spreading means, in which said guiding posts extend perpendicularly from said base portion;
   c) further contacting said graft strip with an impulsive force spreading means; and
   d) providing an impulsive force to said graft strip.

9. The process according to claim 8 wherein said impulsive force is applied to said graft strip in a direction substantially perpendicular to the plane of the impulsive force spreading means.

10. The process according to claim 8 wherein said impulsive force is delivered to said graft strip by the application of an impulsive force to said force spreading means.

11. A process according to claim 8 wherein said impulsive force spreading means is essentially planar in configuration.

12. A process according to claim 11 wherein the planes of the impulsive force spreading means and that of said first horizontal plane are substantially parallel to one another.

13. A process according to claim 8 wherein said impulsive force spreading means is curved in cross section, between 0 and pi/6 radians.

14. A process according to claim 8 wherein said cutting means have edges which are arranged in a parallel configuration with respect to one another.

15. A process according to claim 8 wherein said impulsive force is applied in an effective amount for causing multiple simultaneous incisions along said graft strip wherein said incisions are perpendicular to the length dimension of said graft strip.

16. A process according to claim 8 wherein said cutting means are stationary.

17. A process for rapidly producing a large number of structurally intact, healthy micrografts of follicle-bearing skin tissue useful for surgical implantation which comprises the steps of:
   a) providing at least one graft strip of follicle-bearing tissue;
   b) contacting said graft strip with a plurality of cutting means, wherein said cutting means have cutting edges which coincide on a common first horizontal plane;
   c) further contacting said graft strip with an impulsive forces spreading means; and
   d) providing an impulsive force to said graft strip, wherein the magnitude of said impulsive force is between about 0.1 Newton seconds and 100 Newton seconds.

18. A process for rapidly producing a large number of structurally intact, healthy micrografts of follicle-bearing skin tissue useful for surgical implantation which comprises the steps of:
   a) providing at least one graft strip of follicle-bearing tissue;
   b) contacting said graft strip with a plurality of cutting means, wherein said cutting means have cutting edges which coincide on a common first horizontal plane;
   c) further contacting said graft strip with an impulsive forces spreading means; and
   d) providing an impulsive force to said graft strip, wherein the impulsive force is applied to said graft in a time interval having a duration between about 0.001 seconds and 0.20 seconds.

19. A process for transplantation of hair comprising the step of surgical implantation of at least one hair graft produced in accordance with claim 8 into a human scalp.

20. The process according to claim 8 wherein the direction of growth of the hair follicles is substantially coincident with the parallel cutting means.

* * * * *